United States Patent [19]

Spang et al.

[11] Patent Number: 5,008,397

[45] Date of Patent: Apr. 16, 1991

[54] N-SUBSTITUTED BENZIMIDAZOLE-2-CARBOXANILIDES

[75] Inventors: Peter Spang, St. Ingbert; Peter Neumann, Mannheim; Gerhard Wagenblast, Frankenthal; Hubert Trauth, Dudenhofen, all of Fed. Rep. of Germany

[73] Assignee: BASF Aktiengesellschaft, Ludwigshaften, Fed. Rep. of Germany

[21] Appl. No.: 393,962

[22] Filed: Aug. 15, 1989

[30] Foreign Application Priority Data

Aug. 23, 1988 [DE] Fed. Rep. of Germany ....... 3828537

[51] Int. Cl.$^5$ ............................................. C07D 235/04
[52] U.S. Cl. ..................................... 548/331; 548/327; 548/328
[58] Field of Search ...................... 548/331, 327, 328

[56] References Cited

U.S. PATENT DOCUMENTS

| | | | |
|---|---|---|---|
| 3,661,925 | 5/1972 | McCaully et al. | 548/331 |
| 3,740,413 | 6/1973 | McCaully et al. | 548/331 |
| 3,907,700 | 9/1975 | Grier | 548/331 |
| 4,011,236 | 3/1977 | Grier | 548/331 |

FOREIGN PATENT DOCUMENTS

| | | | |
|---|---|---|---|
| 4011236 | 4/1987 | European Pat. Off. | 548/331 |
| 0284828 | 3/1988 | European Pat. Off. | 548/331 |
| 1517719 | 2/1968 | France | 548/331 |

OTHER PUBLICATIONS

Chemische Berichte, vol. 92, 1959, R. Gompper et al., pp. 550–563.
J. Chem. Soc., Sect. C, 1967, G. Holan et al., pp. 20–25, "2-Trihalogenomethylbenzazoles".
Chemical Abstracts, vol. 101, 1984, p. 594, 22395a.
Chemical Abstracts, vol. 98, 1983, p. 571, 143322r.
Bulletin de la Societe Chimique de France, No. 10, 1966, R. Salle et al., p. 3368.

*Primary Examiner*—Mary C. Lee
*Assistant Examiner*—Robert C. Whittenbaugh
*Attorney, Agent, or Firm*—Oblon, Spivak, McClelland, Maier & Neustadt

[57] ABSTRACT

Compounds of the general formula (I)

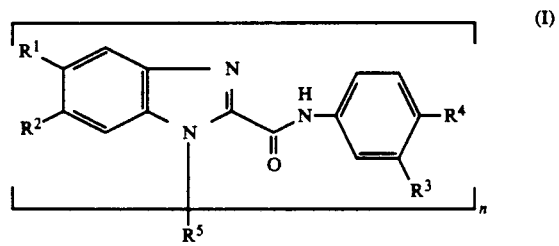

where $R^1$ and $R^2$ are each H, Cl, alkyl, alkoxy, substituted or unsubstituted phenyl or phenylalkyl, $R^3$ and $R^4$ are each H, alkyl, oxaalkyl, alkoxy, oxaalkoxy, substituted or unsubstituted phenyl, phenylalkyl, phenoxy, phenylalkoxy, alkylcarbonylamino, benzoylamino, alkanoyloxy or benzoyloxy, n is 1 or 2 and $R^5$ is — when n is 1-alkyl, hydroxyalkyl, cycloalkyl, alkenyl, oxaalkyl, phenylalkyl or

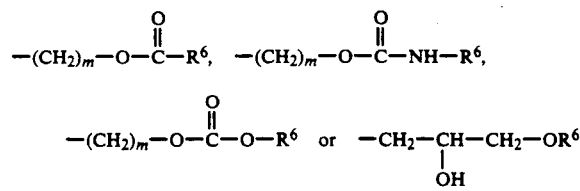

or — when n is 2-akylene, cycloalkylene, alkenylene, oxaalkylene or

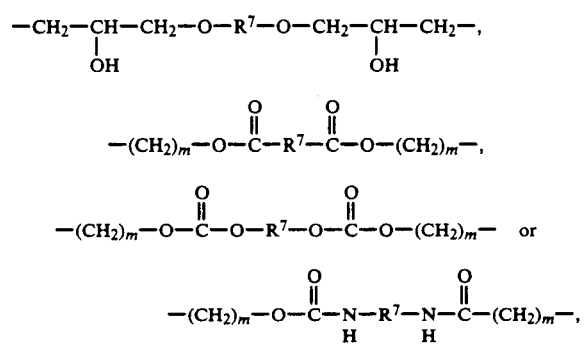

where m is from 2 to 4, $R^6$ is alkyl, alkenyl, cycloalkyl, phenylalkyl, substituted or unsubstituted phenyl or naphthyl, and $R^7$ is alkylene, alkenylene, cycloalkylene, substituted or unsubstituted phenylene, naphthylene, diphenylene,

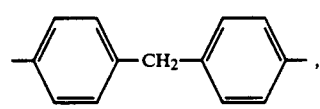

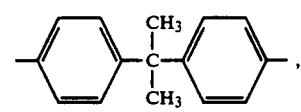

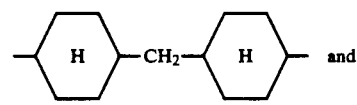 and

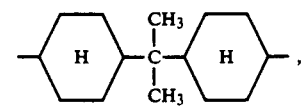

, are effective light stabilizers for organic materials, in particular for polymers.

7 Claims, No Drawings

N-SUBSTITUTED BENZIMIDAZOLE-2-CARBOXANILIDES

U.S. Pat. Nos. 3,907,700 and 4,011,236 already disclose benzimidazole derivatives for use as UV absorbers for plastics. It is true that the N-(benzimidazol-2-yl)-phenylcarboxamides of the formula (X)

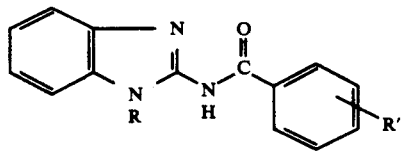

described therein have strong absorption bands in the UV region of from 280 to 350 nm, but their application properties do not meet present-day requirements.

The disadvantages with these compounds are the poor solubility, their migration tendency and their inadequate stabilizing effect, in particular in radiation-sensitive plastics, such as polyurethanes.

It is an object of the present invention to develop light stabilizers for organic materials, in particular for polymers, which do not have the disadvantages of the prior art stabilizers.

We have found that this object is achieved by compounds of the formula (I)

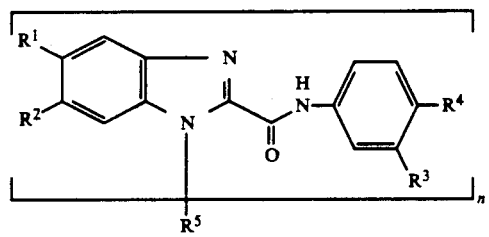

where $R^1$ and $R^2$ are each independently of the other H, Cl, $C_1$-$C_4$-alkyl, $C_1$-$C_4$-alkoxy, unsubstituted or $C_1$-$C_4$-alkyl- or $C_1$-$C_4$-alkoxy-substituted phenyl or $C_7$-$C_9$-phenylalkyl, and $R^4$ are each independently of the other H, $C_1$-$C_{18}$-alkyl, $C_3$-$C_{18}$-alkyl which is interrupted one or more -2- 0.Z. 0050/40120 times by —O—, $C_1$-$C_{18}$-alkoxy, $C_4$-$C_{18}$-alkoxy which is interrupted one or more times by —O—, unsubstituted or $C_1$-$C_4$-alkyl- or $C_1$-$C_4$-alkoxy-substituted phenyl, $C_7$-$C_{15}$-phenylalkyl, phenoxy, $C_7$-$C_{15}$-phenylalkyloxy, $C_1$-$C_{12}$-alkylcarbonylamino, benzoylamino, $C_1$-$C_{12}$-alkanoyloxy or benzoyloxy, or $R^3$ and $R^4$ together are methylenedioxy or ethylenedioxy, n is 1 or 2 and $R^5$ is (a)—when n is 1 —$C_5$-$C_{18}$-alkyl, $C_2$-$C_{10}$-hydroxyalkyl, $C_5$-$C_{12}$-cycloalkyl, $C_2$-$C_{18}$-alkenyl, which cycloalkyl and alkenyl may be substituted by OH, $C_3$-$C_{18}$-alkyl which is interrupted one or more times by —O—, unsubstituted or $C_1$-$C_4$-alkyl- or $C_1$-$C_4$-alkoxy-substituted $C_8$-$C_{15}$-phenylalkyl or a radical of the formula

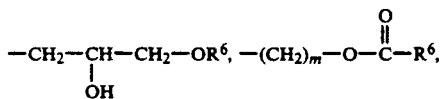

-continued

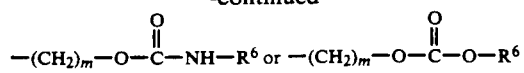

where
m is from 2 to 4 and
$R^6$ is $C_1$-$C_{18}$-alkyl, $C_2$-$C_{18}$-alkenyl, $C_5$-$C_{12}$-cycloalkyl, $C_7$-$C_{15}$-phenylalkyl, unsubstituted or $C_1$-$C_4$-alkyl-, $C_1$-$C_4$-alkoxy- or Cl-substituted phenyl or naphthyl, or (b)—when n is 2 —$C_2$-$C_{10}$-alkylene, $C_5$-$C_{12}$-cycloalkylene, which alkylene and cycloalkylene may be substituted by —OH, $C_4$-$C_{12}$-alkenylene, $C_4$-$C_8$-alkylene which is interrupted one or more times by —O—, or a radical of the formula

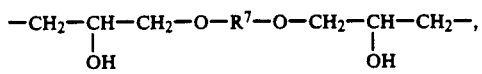

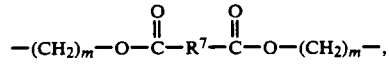

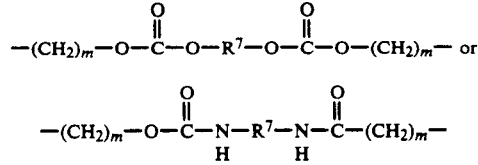

where
$R^7$ is $C_2$-$C_8$-alkylene, $C_2$-$C_8$-alkenylene, $C_5$-$C_{12}$-cycloalkylene, unsubstituted or $C_1$-$C_4$-alkyl- or $C_1$-$C_4$-alkoxysubstituted phenylene, naphthylene, diphenylene or a radical of the formula

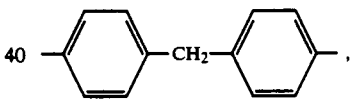

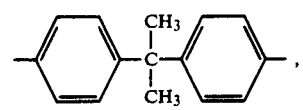

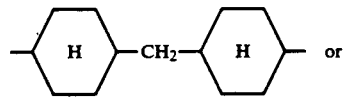

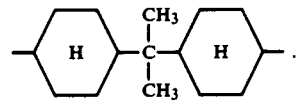

The compounds (I) of the invention are effective light stabilizers for organic materials, for example for a large number of polymers.

The compounds according to the invention not only are effective light stabilizers, but owing to their low volatility at elevated temperatures are also particularly suitable for stabilizing polymers which need to be processed at elevated temperatures.

$R^1$ and $R^2$ are each preferably hydrogen, chlorine, $C_1$-$C_4$-alkyl such as methyl, ethyl, n- and i-propyl, or n-, i- and t-butyl, $C_1$-$C_4$-alkoxy such as methoxy, ethoxy, propoxy and butoxy, phenyl, benzyl, α-methylbenzyl or α,α-dimethylbenzyl.

$R^1$ and $R^2$ are each particularly preferably hydrogen. $R^3$ and $R^4$ are each preferably hydrogen, $C_1$-$C_{12}$-alkyl, $C_3$-$C_{10}$-alkyl which is interrupted one or more times by —O—, $C_1$-$C_{12}$-alkoxy, $C_4$-$C_{12}$-alkoxy which is interrupted one or more times by —O—, $C_7$-$C_9$-phenylalkyl, phenoxy, $C_7$-$C_9$-phenyl alkoxy, $C_1$-$C_{12}$-alkylcarbonylamino, benzoylamino, $C_1$-$C_{12}$-alkanoyloxy or benzoyloxy.

$R^3$ and $R^4$ together can also be methylenedioxy or ethylenedioxy.

In addition to the specific possibilities mentioned for $R^3$ and $R^4$, they can each also be in particular for example:

(α) $C_1$-$C_{12}$-alkyl: methyl, ethyl, n-propyl, i-propyl, n-butyl, 2-butyl, tert-butyl, n-pentyl, tert-pentyl, n-hexyl, n-heptyl, n-octyl, 2-ethylhexyl, n-nonyl, n-decyl and n-dodecyl;

(β) $C_1$-$C_{12}$-alkoxy: methoxy, ethoxy, i-propoxy, n-butoxy, n-pentoxy, i-pentoxy, n-hexoxy, n-heptoxy, n-octoxy, 2-ethylhexoxy, n-nonoxy, n-decoxy and n-dodecoxy;

(γ) benzyloxy, 2-phenylethoxy or 3-phenylpropoxy.

Particular preference is given to compounds (I) where $R^3$ is H and $R^4$ is $C_1$-$C_{12}$-alkyl, $C_1$-$C_{12}$-alkoxy, phenoxy, $C_1$-$C_{12}$-alkylcarbonylamino or $C_1$-$C_{12}$-alkanoyloxy.

The meaning of $R^5$ depends on whether n is 1 or 2. When n is 1, $R^5$ is $C_5$-$C_{18}$-alkyl, $C_2$-$C_{10}$-hydroxyalkyl, $C_5$-$C_{12}$-cycloalkyl, $C_2$-$C_{18}$-alkenyl, $C_3$-$C_{18}$-alkyl which is interrupted one or more times by —O—, unsubstituted or $C_1$-$C_4$-alkyl- or $C_1$-$C_4$-alkoxy-substituted $C_8$-$C_{15}$-phenylalkyl or a radical of the formula

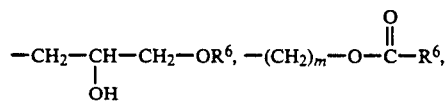

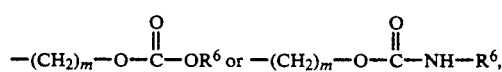

where m is 2, 3 or 4 and $R^6$ is $C_1$-$C_{18}$-alkyl, $C_2$-$C_{18}$-alkenyl, $C_5$-$C_{12}$-cycloalkyl, $C_7$-$C_9$-phenylalkyl, unsubstituted or $C_1$-$C_4$-alkyl- or $C_1$-$C_4$-alkoxy-substituted phenyl or naphthyl.

In this case, $R^5$ is preferably $C_5$-$C_{12}$-alkyl, $C_5$-$C_{12}$-cycloalkyl, $C_2$-$C_4$-hydroxyalkyl such as hydroxyethyl, hydroxypropyl, hydroxyisopropyl or hydroxybutyl, $C_8$ or $C_9$-phenylalkyl, $CH_2CH_2OCH_2CH_3$, $CH_2CH_2OC_4H_9$, $CH_2CH_2OCH_2CH_2OCH_3$, $CH_2CH_2OCH_2CH_2OC_2H_5$, $CH_2CH_2OCH_2CH_2OC_4H_9$,

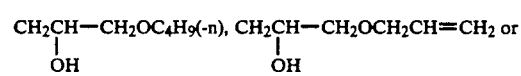

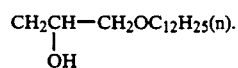

Preferably, m is 2 and $R^6$ is $C_1$-$C_{18}$-alkyl, $C_5$-$C_{12}$-cycloalkyl, $C_1$-$C_{18}$-alkenyl, benzyl, phenylethyl, phenylpropyl, phenyl, $C_1$-$C_4$-alkyl- or $C_1$-$C_4$-alkoxy-substituted phenyl or naphthyl.

If n is 2, $R^5$ is preferably $C_2$-$C_{10}$-alkylene, $C_4$-$C_{12}$-alkenylene, $C_4$-$C_8$-alkylene which is interrupted one or more times by —O— or a divalent radical of the formula

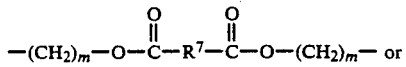

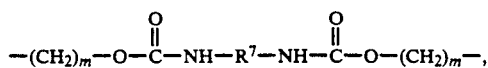

where m is 2, 3 or 4, in particular 2. $R^7$ is preferably $C_2$-$C_8$-alkylene.

The compounds of the formula (I) can be prepared in a conventional manner.

To prepare the compounds of the formula (I), it is preferable to start from benzimidazole-2-carboxanilide derivatives of the formula (II) described in EP-A-0,284,828.

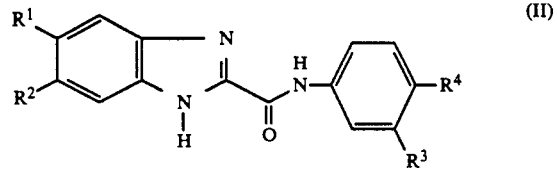

(II)

For instance, the compounds (I) are readily obtainable by reacting anilides of the formula (II) with compounds of the formula (III)

(III)

where

X is a leaving group, such as Cl, Br or

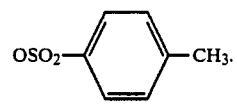

X is preferably Cl or Br. These reactions are carried out under the conditions customary for N-alkylations. Suitable solvents are, for example, dimethylformamide, dimethylacetamide, N-methylpyrrolidone, ethylene glycol diethers and aliphatic ketones, such as acetone or cyclohexanone.

Preference is given to dimethylformamide, N-methylpyrrolidone and cyclohexanone as the reaction media.

Suitable auxiliary bases for these reactions are the customary ones, for example KOH, NaOH, $K_2CO_3$, $Na_2CO_3$, $KHCO_3$, $NaHCO_3$ or else sodium methoxide or sodium ethoxide. Of these, KOH, $K_2CO_3$ and $KHCO_3$ are particularly preferred, depending on the nature of the radical $R_5$ and the leaving group X.

The reaction temperatures are within the range from room temperature to 160° C., preferably from 60° C. to 140° C., in particular from 80° to 110° C.

Compounds of the formula (I) where $R^5$ is the radical —CH$_2$—CH(OH)—CH$_2$—O—R$^6$ can be prepared by reacting anilides of the formula (II) with glycidyl ethers of the formula (IVa):

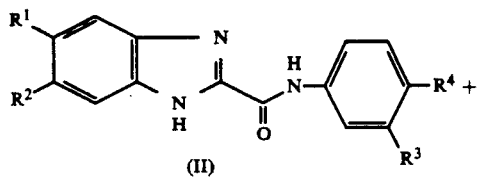
(II)

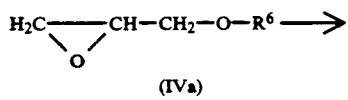
(IVa)

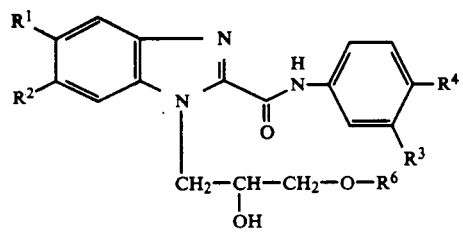

By reacting two equivalents of anilides (II) with 1 mole of diglycidyl ether of the fornula (IVb)

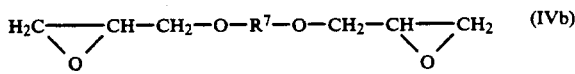
(IVb)

it is similarly possible to prepare compounds (I) where n is 2 and

R$^5$ is —CH$_2$—CH(OH)—CH$_2$—O—R$^7$—O—CH$_2$—CH(OH)—CH$_2$—.

The reaction with (IVa) or (IVb) takes place in inert solvents, for example toluene or dimethylformamide, in the presence of a base, such as piperidine, triethylamine, K$_2$CO$_3$ or Na$_2$CO$_3$, at from 50 to 120° C.

Compounds of the formula (I) where is one of the radicals

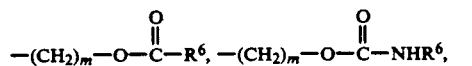

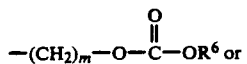

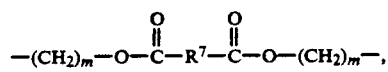

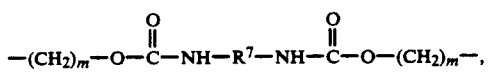

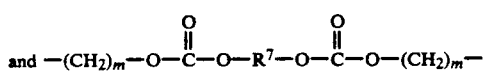

can be synthesized by reacting anilides of the formula (V)

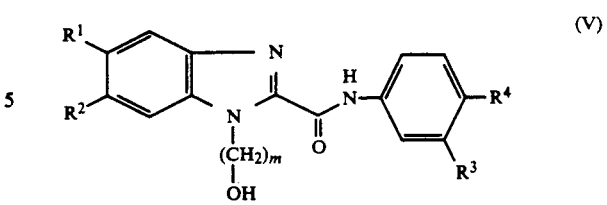
(V)

either with (a) mono- or dicarboxylic acid derivatives of the formula (VIa) or (VIb)

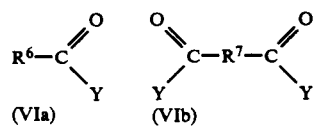
(VIa)  (VIb)

where
Y is Cl, OCH$_3$, OC$_2$H$_5$ or OC$_6$H$_5$, or with
(b) mono- or diisocyanates of the formula (VIIa) or (VIIb)

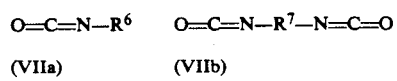
(VIIa)   (VIIb)

or with (c) mono- or dichloroformic esters of the formula (VIIIa) or (VIIIb)

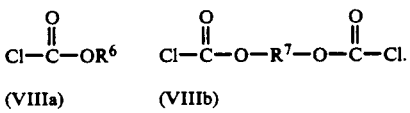
(VIIIa)   (VIIIb)

Compounds (I) are incorporated into polymers in a conventional manner. Incorporation can be effected for example by mixing the compounds with or without further additives into the melt by customary methods before or during molding, or else by applying the dissolved or dispersed compounds to the polymer directly or by mixing into a solution, suspension or emulsion of the polymer, the solvent being subsequently removable if necessary by evaporation.

Suitable polymers are for example: polyolefins, polystyrene, styrene polymers, halogen-containing vinyl polymers, polyacrylates, polymethacrylates, polyacrylamides, polyacrylonitrile, polyvinyl alcohol and acyl derivatives thereof, polyacetates, polyalkylene oxides, polyphenylene oxides, polyurethanes, polyureas, polysulfones, polyamides, polyesters, polycarbonates, crosslinked polymers from aldehydes and phenols, ureas or melamine, unsaturated polyester resins, alkyd resins and thermosetting and thermoplastic acrylic resins.

The present invention thus also provides stabilized organic materials, in particular synthetic polymers, which contain from 0.05 to 10, preferably from 0.1 to 5, by weight, based on the material to be stabilized, of one or more compounds of the formula I.

Owing to their very low volatility, the compounds according to the invention are highly suitable for stabilizing polyesters such as, for example, polyethylene terephthalate, polybutylene terephthalate or copolymers thereof, polycarbonates, e.g. of bisphenol A and phosgene, or copolymers thereof, polyamides, for example nylon-6, nylon-6,6, nylon-6,10, etc., copolymers of MF-and UF-resins, hot-crosslinkable and thermoplastic acrylic resins, and polyurethanes.

Compounds (I) are very particularly suitable for stabilizing coating formulations of such polymers.

The materials thus stabilized can be converted into the forms customary for use, for example into films, fibers, ribbons or profiles, or be used for the production of binders for coatings, adhesives, cements or molding compositions.

In practice, the compounds of the formula I can be used together with from 0.1 to 5, preferably from 0.5 to 3, % by weight of further customary additives, such as antioxidants, further light stabilizers or mixtures thereof.

Such customary additives are for example: anti-oxidants, UV absorbers and light stabilizers such as 2-(2'-hydroxyphenyl)benzotriazoles, 2,4-bis(2,-hydroxyphenyl)-6-alkyl-s-triazines, 2-hydroxybenzophenones,1,3-bis(2'-hydroxybenzoyl)benzenes, esters of substituted or unsubstituted benzoic acids, acrylates, also nickel compounds, sterically hindered amines, metal deactivators, phosphites, peroxide-destroying compounds, polyamide stabilizers, basic costabilizers, nucleating agents and other additives such as plasticizers, lubricants, emulsifiers, fillers, carbon black, kaolin, talc, glass fibers, pigments, fluorescent whitening agents, flameproofing agents and antistats.

The compounds of the formula (I) are highly suitable for protecting ABS polymers and in particular polyurethanes derived from polyethers, polyesters and polybutadiene having terminal hydroxyl groups and aliphatic or aromatic polyisocyanates, and intermediates therefor, against degradation by heat and in particular by the action of light.

An improved stabilizing effect is obtained on using in addition a known antioxidant, for example a compound based on sterically hindered phenols or a sulfur- or phosphorus-containing costabilizer.

Suitable phenolic antioxidants of this type are for example 2,6-di-tert-but-Yl-4-methylphenol, n-octadecyl β-(3,5-di-tert-butyl-4-hydroxyphenyl) propionate, 1,1,3-tris(2-methyl-4-hydroxy-5-tert-butylphenyl) butane, 1,3,5-trimethyl-2,4,6-tris (3,5-di-tert-butyl-4-hydroxybenzyl)benzene, 1,3,5-tris(3,5-di-tert-butyl-4-hydroxybenzyl) isocyanurate, 1,3,5-tris[3,5-di-tert-butyl-4-hydroxyphenylpropionyloxyethyl]isocyanurate, 1,3,5-tris(2,6-dimethyl-3-hydroxy-4-tert-butylbenzyl) isocyanurate and pentaerythritol tetrakis[β-(3,5-di-tert-butyl4-hydroxyphenyl) propionate].

Suitable phosphorus-containing antioxidants are for example: tris(nonylphenyl) phosphite, distearyl pentaerythritol diphosphite, tris(2,4-di-tert-butylphenyl) phosphite, tris(2-tert-butyl-4-methylphenyl) phosphite, bis(2,4-di-tert-butylphenyl) pentaerythritol diphosphite and tetrakis(2,4-di-tert-butylphenyl)-4,4'-diphenylene diphosphite.

Suitable sulfur-containing antioxidants are for example dilauryl thiodipropionate, dimyristyl thiodipropionate, distearyl thiodipropionate, pentaerythritol tetrakis (β-laurylthiopropionate) and pentaerythritol tetrakis(β-hexylthiopropionate).

Particularly good stabilization is obtained on adding to the compounds of the formula (I) at least one light stabilizer of the class of compounds of sterically hindered amines in a customary concentration.

Suitable sterically hindered amines are for example: bis(2,2,6,6-tetramethylpiperidyl) sebacate, bis(1,2,2,6,6-pentamethylpiperidyl) sebacate, the condensation product of 1-hydroxyethyl-2,2,6,6-tetramethyl-4-hydroxypiperidine and succinic acid, the condensation product of N,N'-(2,2,6,6-tetramethylpiperidyl)hexamethylenediamine and 4-tert-octylamino-2,6-dichloro1,3,5-s-triazine, tris(2,2,6,6-tetramethylpiperidyl) nitrilotriacetate, tetrakis(2,2,6,6-tetramethyl-4-piperidyl)-1,2,3,4-butanetetracarboxylic acid, 1,1'-(1,2-ethanediyl)bis(3,3,5,5-tetramethylpiperazinone), and the condensation products of 4-amino-2,2,6,6-tetramethylpiperidines and tetramethylolacetylenediureas.

Particularly good stabilization of polyurethanes is obtained on stabilizing the polyurethane with a mixture of one or more compounds of the formula (I), one or more of the abovementioned antioxidants, and one or more sterically hindered amine compounds.

The Examples which follow additionally illustrate the invention.

(A) Preparation Examples

EXAMPLE 1

14.1 g (0.05 mol) of 4'-ethoxybenzimidazole-2-carboxanilide of the formula

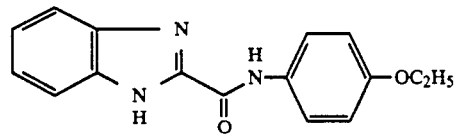

and 8.3 g (0.06 mol) of K₂CO₃ were suspended together with 9.9 g (0.06 mol) of 1-bromohexane in 30 ml of dimethylformamide, and the suspension was stirred at 85°-90° C. for 3 hours.

The hot reaction mixture was then filtered, and the filtrate was evaporated down under reduced pressure. The oily residue was recrystallized from about 120 ml of methanol. Yield: 14.0 g of colorless product of the formula

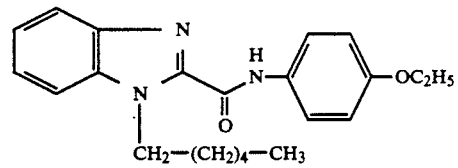

Melting point: 72°-73° C.

Analysis: $C_{22}H_{27}N_3O_2$ (365.5); Calculated: C 72.3; H 7.44; N 11.49; O 8.76; Found: C 72.4; H 7.6; N 11.1; O 8.9.

UV: $\lambda_{max}$ [nm] ($\epsilon \cdot 10^{-3}$)=306 (20.5) in $CH_3OH$.

EXAMPLE 2

14.1 g (0.05 mol) of 4'-ethoxybenzimidazole-2-carboxanilide, 7.0 g (0.07 mol) of KHCO₃ and 13.5 g (0.07 mol) of 1-bromooctane were heated in 25 ml of dimethylformamide at 100°-105° C. for 6.5 hours. The hot reaction solution was then filtered to remove the precipitated NaBr. The solvent was drawn off, and the residue was recrystallized from methanol (about 100 ml). Yield: 14.8 g of colorless crystals of the product of the formula

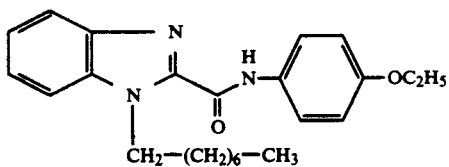

Melting point: 67°-68° C.

Analysis: $C_{24}H_{31}N_3O_2$ (393.6); Calculated: C 73.28; H 7.90; N 10.68; O 8.14; Found: C 73.2; H 7.8; N 10.4; O 8.2;

UV: $\lambda_{max}$ [nm] $(\epsilon \cdot 10^{-3}) = 305$ (20.2).

EXAMPLES 3 TO 10

The method of Example 1 or 2 was applied to appropriately substituted benzimidazole-2-carboxanilides of the formula (II) and the corresponding bromine or chlorine compounds of the formula (III) to prepare the compounds (I) indicated in Table 1.

TABLE 1

| Example | Compound (I) | mp [°C.] | Analysis | | | | UV (CH₃OH) $\lambda_{max}$ [nm] ($\epsilon \cdot 10^{-3}$) |
|---|---|---|---|---|---|---|---|
| | | | | C | H | N | O | |
| 3 | (benzimidazole-carboxanilide with N-CH₂-CH(C₂H₅)-(CH₂)₃-CH₃ and p-OC₂H₅) | 80-82 | c. <br> f. | 73.28 <br> 73.2 | 7.90 <br> 8.1 | 10.68 <br> 10.6 | 8.14 <br> 8.1 | 305 <br> (21.5) |
| 4 | (benzimidazole-carboxanilide with N-CH₂-(CH₂)₁₀-CH₃ and p-OC₂H₅) | 70-71 | c. <br> f. | 74.83 <br> 75.0 | 8.69 <br> 8.8 | 9.35 <br> 8.9 | 7.13 <br> 7.3 | 305 <br> (19.7) |
| 5 | (benzimidazole-carboxanilide with N-C(CH₃)=CH₂ and p-OCH₃) | 113 | c. <br> f. | 71.0 <br> 70.9 | 5.92 <br> 6.0 | 13.08 <br> 13.2 | 9.97 <br> 9.9 | 306 <br> (20.8) |
| 6 | (benzimidazole-carboxanilide with N-C(CH₃)=CH₂ and p-OC₂H₅) | 107-108 | c. <br> f. | 71.64 <br> 71.6 | 6.27 <br> 6.5 | 12.54 <br> 12.5 | 9.55 <br> 9.6 | 307 <br> (20.9) |
| 7 | (5-H₅C₂O-benzimidazole-carboxanilide with N-CH₂-(CH₂)₄-CH₃ and p-OC₂H₅) | 87 | c. <br> f. | 70.41 <br> 70.3 | 7.59 <br> 7.6 | 10.27 <br> 10.2 | 11.73 <br> 11.7 | 323 <br> (21.7) |
| 8 | (benzimidazole-carboxanilide with N-CH₂CH₂OC₂H₅ and p-OC₂H₅) | 88-89 | c. <br> f. | 68.0 <br> 68.1 | 6.52 <br> 6.5 | 11.9 <br> 11.7 | 13.6 <br> 13.4 | 302 <br> (20.2) |

TABLE 1-continued

| Example | Compound (1) | mp [°C.] | Analysis C | H | N | O | UV (CH₃OH) $\lambda_{max}$ [nm] ($\epsilon \cdot 10^{-3}$) |
|---|---|---|---|---|---|---|---|
| 9 | [structure: 4,5-dimethyl benzimidazole with N-CH₂CH₂OC₂H₅ and C(=O)NH-C₆H₄-OC₂H₅] | 139 | c. 69.29<br>f. 69.4 | 7.09<br>6.8 | 11.02<br>11.0 | 12.6<br>12.5 | 315<br>(23.1) |
| 10 | [structure: ethoxy benzimidazole with N-CH₂CH₂OC₂H₅ and C(=O)NH-C₆H₄-OC₂H₅*] | 113 | c. 66.50<br>f. 66.4 | 6.81<br>6.9 | 10.57<br>10.5 | 16.12<br>16.0 | 321<br>(22.3) |

*Isomeric mixtures of 5- and 6-ethoxybenzimidazole derivatives

EXAMPLE 11

28.1 g (0.1 mol) of 4'-ethoxybenzimidazole-2-carboxanilide were suspended together with 14.1 g of 1,5-dichloropentane and 20.7 g of K₂CO₃ in 60 ml of dimethylformamide and heated at 100°–105° C. for 11.5 hours. The hot reaction mixture was filtered, and the filtered residue was washed with dimethylformamide. After the solvent had been drawn off under reduced pressure, the residue was dissolved in hot methanol. On cooling down, colorless crystals were precipitated, which were filtered off with suction and washed with a little methanol. Yield: 5.1 g of the product of the formula

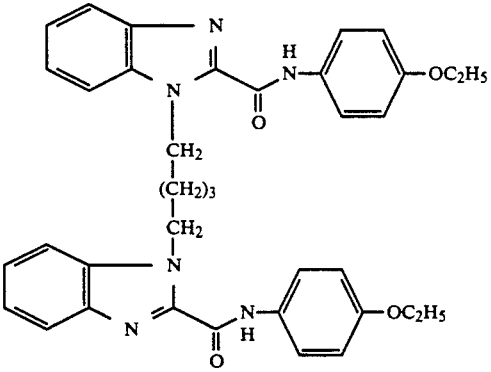

Melting point: 163°–165° C.
Analysis: C₃₇ H₃₈ N₆ O₄ (630.7); Calculated: C 70.47; H 6.08; N 13.33; O 10.15; Found: C 70.1; H 6.1; N 13.1; O 10.2.
UV: $\lambda_{max}$ [nm] ($\epsilon \cdot 10^{-3}$) = 305 (36.6).

EXAMPLES 12 TO 15

The method described in Example 11 was used to react the corresponding benzimidazole-2-carboxanilide of the formula (II) with 2-bromoethanol or 4-chlorobutanol to synthesize the hydroxy-functionalized compounds of the formula (V) listed below in Table 2.

TABLE 2

| Example No. | Compound (I) or (V) | m.p. [°C.] | Analyse C | H | N | O | UV (CH₃OH) $\lambda_{max}$ [nm] ($\epsilon \cdot -3$) |
|---|---|---|---|---|---|---|---|
| 12 | [structure: benzimidazole with N-CH₂CH₂-OH and C(=O)NH-C₆H₅] | 177–178 | c. 68.33<br>f. 68.1 | 5.34<br>5.5 | 14.95<br>14.6 | 11.38<br>11.4 | 303<br>(21.1) |

TABLE 2-continued

| Example No. | Compound (I) or (V) | m.p. [°C] | Analyse C | H | N | O | UV (CH₃OH) $\lambda_{max}$ [nm] ($\epsilon \cdot -3$) |
|---|---|---|---|---|---|---|---|
| 13 | ![structure 13] | 213–214 | c. 69.9<br>f. 69.8 | 6.15<br>6.6 | 13.59<br>13.5 | 10.36<br>10.5 | 315<br>(23.6) |
| 14 | ![structure 14] | 146–147 | c. 66.46<br>f. 66.3 | 5.85<br>5.9 | 12.92<br>13.0 | 14.77<br>14.8 | 306<br>(21.0) |
| 15 | ![structure 15] | 123–125 | c. 68.0<br>f. 68.0 | 6.52<br>6.7 | 11.90<br>11.8 | 13.60<br>13.4 | 307<br>(22.2) |

EXAMPLE 16

7.2 g of pivaloyl chloride were added dropwise to a solution of 16.3 g (0.05 mol) of the compound of Example 14 in 60 ml of dry pyridine at 20°–35° C. After 2 hours of stirring at 50° C., the reaction solution was poured onto 1 l of ice-water, 100 ml of concentrated hydrochloric acid were added, and the mixture was stirred for 0.5 hours. The precipitate formed was filtered off with suction and washed with ice-water, methanol and naphtha. Yield: 18.0 g of a colorless solid of the formula

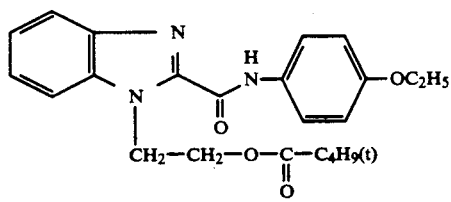

Melting point: 139°–140° C.
Analysis: C₂₃ H₂₇ N₃ O₄ (409.5); Calculated: C 67.48; H 6.61; N 10.27; O 15.64; Found: C 67.5; H 6.8; N 10.2; O 15.3.
UV: $\lambda_{max}$ [nm] ($\epsilon \cdot 10^{-3}$)=308(20.4).

EXAMPLE 17

Example 16 was repeated to react 16.3 g of the compound of Example 14 with 8.5 g of p-toluoyl chloride. Recrystallization from ethanol gave 17.6 g of colorless crystals of the compound of the formula

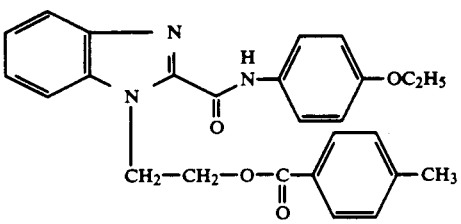

and melting point; 150° C.
Analysis: C₂₆ H₂₅ N₃ O₄ (443.5); Calculated: C 70.42; H 5.65; N 9.48; O 14.44; Found: C 70.8; H 5.8; N 9.1; O 14.3.
UV: $\lambda_{max}$ [nm] ($\epsilon \cdot 10^{-3}$)=302 (19.4).

EXAMPLE 18

Example 17 was repeated to react 19.5 g of the compound of Example 14 with 5.6 g of edipoyl dichloride. The reaction time was 4.5 hours. Working up and recrystallization of ethanol gave 17.8 g of a white solid of the formula

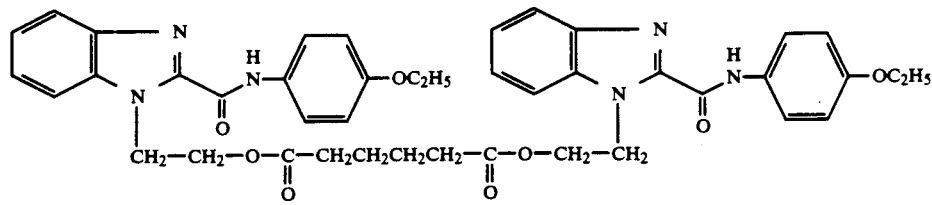

and melting point: 145°–147° C.

Analysis: $C_{42} H_{44} N_6 O_8$ (760.8); Calculated: C 66.31; H 5.8; N 11.5; O 16.84; Found: C 66.4; H 5.9; N 10.9; O 16.7.

UV: $\lambda_{max}$ [nm] ($\epsilon \cdot 10^{-3}$) = 312 (40.5).

EXAMPLE 19

16.3 g of 1-hydroxyethyl-4'-ethoxybenzimidazole-2-carboxanilide (Example 14) were dissolved in 150 ml of dry pyridine. 6.5 g of methacryloyl chloride were added dropwise at 0°–5° C. and stirred in at room temperature for 6.5 hours. The reaction mixture was poured onto 800 ml of ice-water and 100 ml of concentrated hydrochloric acid, and the precipitate formed was filtered off with suction and washed with water. The crude product obtained was dissolved in hot acetone and treated with active charcoal and bleaching earth. After filtration, the solvent was drawn off under reduced pressure at 60°–70° C., leaving 12.8 g of a waxy slightly yellow product of the formula

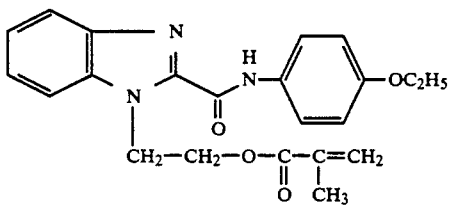

Analysis: $C_{22} H_{23} N_3 O_4$ (393.4); Calculated: C 67.16; H 5.89; N 10.68; O 16.27; Found: C 66.6; H 5.9; N 10.3; O 16.9.

UV: $\lambda_{max}$ [nm] ($\epsilon \cdot 10^{-3}$) = 305 (18.5).

EXAMPLE 20

The method described in Example 16 was used to react 16.3 g of 1-hydroxyethyl-4'-ethoxy-benzimidazole-2-carboxanilide (Example 14) with 15.4 g of palmitoyl chloride. The crude product was dissolved in 500 ml of hot acetone and purified with active charcoal and bleaching earth. Cooling brought down 26.0 g of colorless crystals of the formula

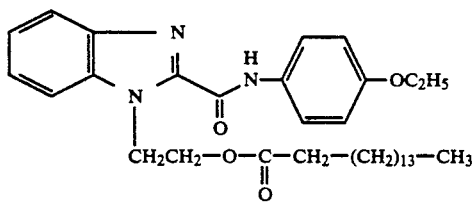

Melting point: 73°–76° C.

Analysis: $C_{34} H_{49} N_3 O_4$ (563.8); Calculated: C 72.43; H 8.80; N 7.45; O 11.35; Found: C 72.9; H 9.2; N 6.7; O 11.5

UV: $\lambda_{max}$ [nm] ($\epsilon \cdot 10^{-3}$) = 305 (18.0).

EXAMPLE 21

Example 20 was repeated using oleyl chloride to obtain 25.5 g of a pale yellow only oil product of the formula

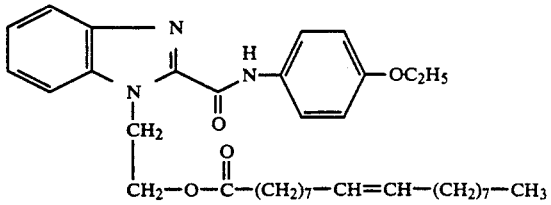

which with time solidifies into wax.

Analysis: $C_{36} H_{51} N_3 O_4$ (598.8); Calculated: C 73.31; H 8.72; N 7.12; O 10.85; Found: C 73.5; H 8.7; N 6.6; O 11.1.

UV: $\lambda_{max}$ [nm] ($\epsilon \cdot 10^{-3}$) = 307 (21.1).

EXAMPLE 22

7.0 g of n-butyl isocyanate were added dropwise to a solution of 19.5 g of the compound of Example 14 and 6.1 g of triethylamine in 70 ml of dimethylformamide at room temperature. The mixture was subsequently stirred at 60°–65° C. for 4 hours. The solvent was distilled off under reduced pressure and the residue was recrystallized from ethanol, giving 19.9 g of a colorless product of the formula

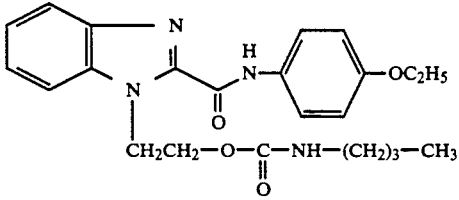

and melting point 123°–124° C.

Analysis: $C_{23} H_{28} N_4 O_4$ (424.5); Calculated: C 65.10; H 6.61; N 13.21; O 15.10; Found: C 65.3; H 6.8; N 13.2; O 15.2.

UV: $\lambda_{max}$ [nm] ($\epsilon \cdot 10^{-3}$) = 308 (21.3).

EXAMPLE 23

Example 21 was repeated using phenyl isocyanate in place of n-butyl isocyanate to obtain the urethane of the formula

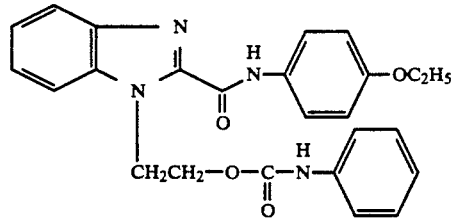

Melting point: 148°–150° C.

Analysis: $C_{25} H_{24} N_4 O_4$ (444.5); Calculated: C 67.57; H 5.41; N 12.61; O 14.14; Found: C 67.5; H 5.6; N 12.6; O 14.4.

UV: $\lambda_{max}$ [nm] ($\epsilon \cdot 10^{-3}$) = 307 (21.1).

EXAMPLE 24

19.5 g of 1-hydroxyethyl-4'-ethoxybenzimidazole-2-carboxanilide were dissolved together with 6.1 g of triethylamine in 100 ml of dimethylformamide, and 5.1 g of hexamethylene diisocyanate were added dropwise at room temperature. The reaction mixture was stirred at 75°–80° C. for 5.5 hours, cooled down to 40° C. and then added to 350 ml of methanol. The precipitate formed was filtered off with suction and washed with methanol and a little acetone. Yield: 21.1 g of product of the formula

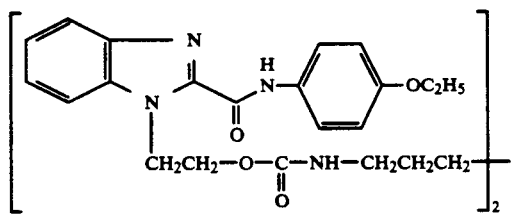

Melting point: 191°–193° C.

Analysis: $C_{44} H_{50} N_8 O_8$ (818.8); Calculated: C 64.55; H 6.12; N 13.69; O 15.64; Found: C 64.4; H 6.4; N 13.7; O 15.8.

EXAMPLE 25

A suspension of 28.1 g of 4′-ethoxybenzimidazole-2-carboxanilide, 14.3 g of $K_2CO_3$ and 14.3 g of n-butyl glycidyl ether in 200 ml of dimethylformamide was heated at 100°–105° C. for 20 hours with stirring. The reaction mixture was filtered, and the filtrate was concentrated under reduced pressure. The oily residue was dissolved in 450 ml of hot ethanol, and the solution was treated with active charcoal and filtered. Cooling produced 14.2 g of colorless crystals of the formula

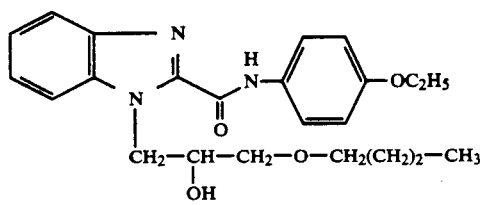

Melting point: 101°–102° C.

Analysis: $C_{23} H_{29} N_3 O_4$ (411.5); Calculated: C 67.13; H 7.14; N 10.21; O 15.52; Found: C 67.3; H 7.1; N 10.2; O 15.6.

EXAMPLE 26

28.1 g of 4′-ethoxybenzimidazole-2-carboxanilide were heated together with 13.8 g of $K_2CO_3$ and 14.6 g of allyl glycidyl ether at 100°–105° C. for 5 hours. The reaction mixture was filtered while still hot. The filtrate was mixed with active charcoal, stirred at 80° C. for 15 minutes and filtered. The solvent was distilled off to leave a resinous residue which was recrystallized from 600 ml of ethanol. Yield: 23.1 g of a colorless solid of the formula

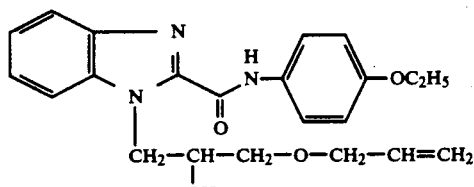

Melting point: 124°–126° C.

Analysis: $C_{22} H_{25} N_3 O_4$ (395.4); Calculated: C 66.84; H 6.33; N 10.63; O 16.20; Found: C 66.6; H 6.5; N 10.7; O 16.3.

EXAMPLE 27

Example 26 was repeated with n-dodecyl glycidyl ether, affording 24.5 g of colorless crystals (melting point 79°–80° C.) of the formula

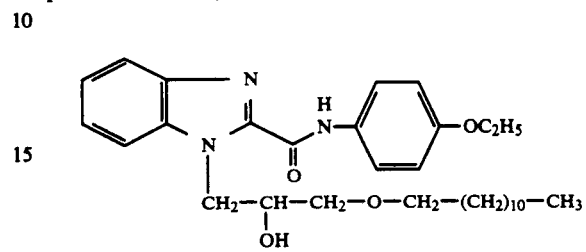

Analysis: $C_{31} H_{45} N_3 O_4$ (523.6); Calculated: C 71.09; H 8.66; N 8.02; O 12.23; Found: C 70.6; H 8.5; N 7.8; O 12.2.

EXAMPLE 28

Example 2 was repeated on 4′-ethoxybenzimidazole-2-carboxanilide and a 1:1 mixture of 1-dodecyl chloride and 1-tetradecyl chloride, affording a 1:1 product mixture of the formula

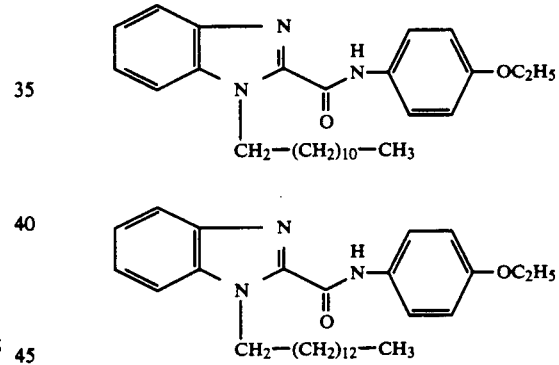

in the form of colorless crystals of melting point 59°–60° C.

Analysis: $C_{28}H_{29}N_3O_2/C_{30}H_{43}N_3O_2$; Calculated: C 75.12; H 8.91; N 9.06; O 6.90; Found: C 74.9; H 9.0; N 9.2; O 6.9.

UV: $\lambda_{max}$ [nm] ($\epsilon \cdot 10^{-3}$) = 312 (22.6).

EXAMPLE 29

84.3 g (0.3 mol) of 4′-ethoxybenzimidazole-2-carboxanilide were stirred together with 58 g (0.42 mol) of $K_2CO_3$ and 63.6 g (0.36 mol) of isodecyl chloride in 300 ml of dimethylformamide at 120°–125° C. for 4.5 hours. The reaction mixture was filtered while hot, the residue was washed with 100 ml of dimethylformamide, and the combined filtrates were concentrated under reduced pressure. The oily residue was taken up in 300 ml of ethyl acetate and purified with active charcoal and bleaching earth. The solvent was distilled off under reduced pressure to leave 122 g of a pale yellow oil of the product of the formula

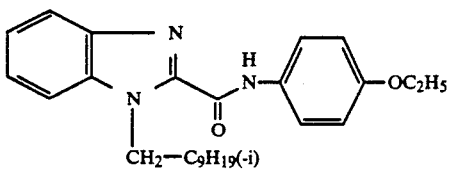

Analysis: $C_{26}H_{35}N_3O_2$ (421.3); Calculated: C 74.05; H 8.38; N 9.67; O 7.60; Found: C 74.1; H 8.6; N 9.9; O 7.8; UV: $\lambda_{max}$ [nm] ($\epsilon \cdot 10^{-3}$)=311 (23.1).

EXAMPLE 30

Example 29 was repeated using 4'-ethoxybenzimidazole-2-carboxanilide and 1-chloro-2,4,6-trioxadecane to obtain the product of the formula

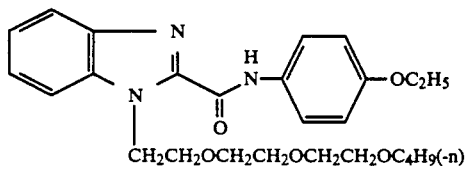

in the form of a pale yellow oil.
$C_{26}H_{35}N_3O_5$ (469.3);
UV: $\lambda_{max}$ [nm] ($\epsilon \cdot 10^{-3}$)=312 (21.0).

EXAMPLE 31

Example 29 was repeated using Cl—CH$_2$—CH$_2$(—O—CH$_2$CH$_2$—)$_2$OC$_2$H$_5$, affording the product of the formula

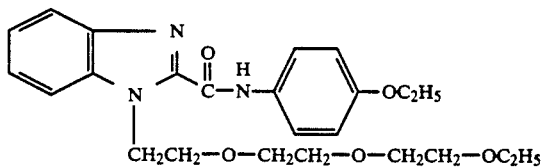

in the form of a yellow oil.
$C_{24}H_{31}N_3O_2$ (441.3); Calculated: C 65.35; H 7.1; N 9.5; O 18.1; Found: C 61.1; H 7.1; N 9.91; O 18.3.
UV: $\lambda_{max}$ [nm] ($\epsilon \cdot 10^{-3}$)=312 (22.6).

EXAMPLE 32

Example 29 was repeated using Cl—CH$_2$—CH$_2$O—CH$_2$CH$_2$ 2OCH$_3$, affording the product of the formula

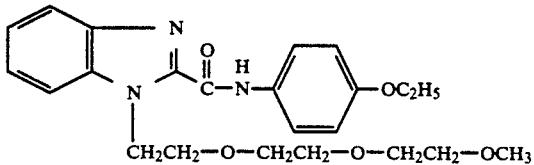

as a pale yellow oil.
$C_{32}H_{29}N_3O_5$ (427.5); Calculated: C 64.6; H 6.8; N 9.8; O 18.7; Found: C 64.1; H 6.8; N 10.4; O 18.7.
UV: $\lambda_{max}$ [nm] ($\epsilon \cdot 10^{31\ 3}$)=312 (20.7).

EXAMPLE 33

Example 29 was repeated using 2-n-hexoxyethyl chloride, affording the product of the formula

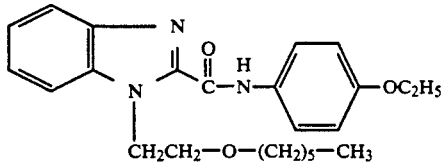

as a colorless solid of melting point 66°–67° C. (from methanol).
$C_{24}H_{31}N_3O_3$ (409.5); Calculated: C 70.4; H 7.6; N 10.3; O 11.7; Found: C 70.3; H 7.8; N 10.3; O 11.9.
UV: $\lambda_{max}$ [nm] ($\epsilon \cdot 10^{-3}$)=305 (25.5).

EXAMPLE 34

Example 29 was repeated, using 4'-ethoxybenzimidazole-2-carboxanilide and isononyl chloride, affording the product of the formula

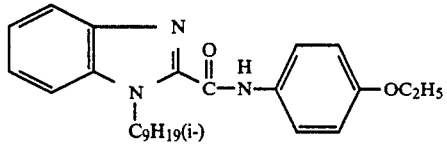

as a colorless solid of melting point 120°–125° C.
$C_{25}H_{33}N_3O_2$ (407.5); Calculated: C 73.7; H 8.2; N 10.3; O 7.9; Found: C 73.7; H 8.5; N 10.4; O 8.0.
UV: $\lambda_{max}$ [nm] ($\epsilon \cdot 10^{-3}$)=311 (22.8).

EXAMPLE 35

Example 29 was repeated using 4'-ethoxybenzimidazole-2-carboxanilide and oleyl chloride to obtain the product of the formula

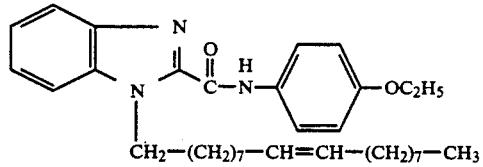

as a pale yellow oil.
$C_{34}H_{49}N_3O_2$ (531.4); Calculated: C 76.8; H 9.3; N 7.9; O 6.0; Found: C 76.3; H 9.3; N 8.0; O 6.2.
UV: $\lambda_{max}$ [nm] ($\epsilon \cdot 10^{-3}$)=311 (22.0).

EXAMPLE 36

Example 29 was repeated using 4'-ethoxybenzimidazole-2-carboxanilide and isotridecyl chloride to obtain the product of the formula

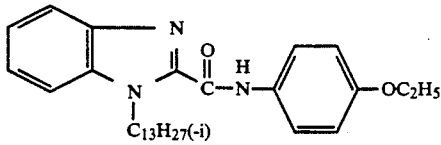

$C_{29}H_{41}N_3O_2$ (463.6); Calculated: C 75.1; H 8.9; N 9.1; O 6.9; Found: C 75.3; H 9.1; N 8.9; O 7.2.
UV: $\lambda_{max}$ [nm] ($\epsilon \cdot 10^{-3}$)=312 (20.5).

EXAMPLE 37

Example 29 was repeated using Cl—$CH_2$—$CH_2$(—O—$CH_2CH_2$—)$_3OC_2H_5$ to obtain the product of the formula

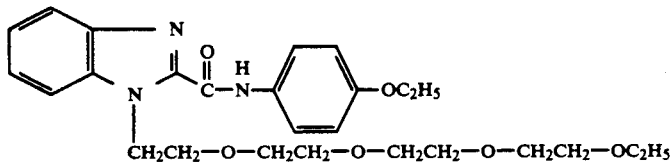

$CH_2CH_2$—O—$CH_2CH_2$—O—$CH_2CH_2$—O—$CH_2CH_2$—$OC_2H_5$ $C_{26}H_{35}N_3O_6$ (485.3); Calculated: C 64.3; H 7.3; N 8.7; O 19.8; Found: C 63.4; H 7.1; N 9.0; O 19.7.
UV: $\lambda_{max}$ [nm] ($\epsilon \cdot 10^{-3}$)=311 (20.7).

EXAMPLE 38

Example 29 was repeated using Cl—$CH_2$—$CH_2OCH_2CH_{2\ 3}OCH_3$ to obtain the product of the formula

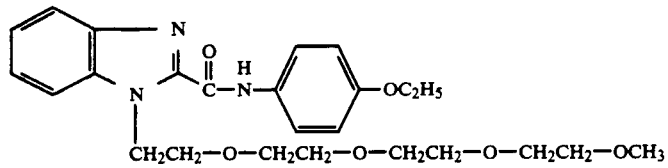

$CH_2CH_2$—O—$CH_2CH_2$—O—$CH_2CH_2$—O—$CH_2CH_2$—$OCH_3$ as a pale yellow oil.
$C_{25}H_{33}N_3O_6$ (471.5); Calculated: C 63.7; H 7.1; N 8.9; O 20.4; Found: C 63.1; H 7.0; N 8.8; O 20.6.
UV: $\lambda_{max}$ [nm] ($\epsilon \cdot 10^{-3}$)=311 (20.4).

(B) Application Examples

APPLICATION EXAMPLE 1

Light-stabilizing action in polyurethane

Preparation of polyurethane samples for irradiation tests

A polyol component composed of 41.9 parts of a polyetherol of OH number 29.0, obtained by addition of propylene oxide and ethylene oxide onto propylene glycol and having approximately 84% of primary hydroxyl groups, and 42.5 parts of a polyetherol of OH number 27.0, obtained by addition of propylene oxide and ethylene oxide onto trimethylolpropane and having approximately 88% of primary hydroxyl groups, and 8.1 parts of 1,4-butanediol and 1.724 parts of a 25% strength solution of diazabicyclooctane in 1,4-butanediol and 0.016 part of dibutyltin dilaurate and 0.1 part of the silicone stabilizer OS 710 from Bayer and 5.49 parts of Frigen 11 and 0.17 part of water was admixed with the stated stabilizers and foamed in a mixing ratio of 100 : 48.5 with a prepolymer having an isocyanate group content of 23.0% at a component and mold temperature of 25° C. to form test sheets. The NCO prepolymer was prepared from 87.17 parts of 4,4'-diphenylmethane diisocyanate and 4.83 parts of a polyetherol of OH number 250, obtained by addition of propylene oxide onto propylene glycol, and 8.0 parts of dipropylene glycol.

The samples were irradiated in a Xenotest ® 450 and rated in terms of the yellowness index (YI) of ASTM D 1925. The results are given below.

TABLE 3

| Stabilizer | Concentration [%] | YI of ASTM D 1925 0 h | YI of ASTM D 1925 48 h |
|---|---|---|---|
| 3.1 Control | — | 1.4 | 24.1 |
| 3.2 Compound of Example 1 | 1.0 | 1.6 | 12.9 |
| 3.3 Compound of Example 2 | 1.0 | 3.0 | 12.0 |
| 3.4 Compound of Example 9 | 1.0 | 3.4 | 15.0 |
| 3.5 Combination of: 2-(2'-Hydroxy-5'-methylphenyl)-benzotriazole | 0.5 | | |
| + A* | 0.5 | 2.7 | 14.8 |
| + Triethylene glycol bis-3-(3-t-butyl-4-hydroxy-5-methylphenyl)propionate | 0.25 | | |

*A =

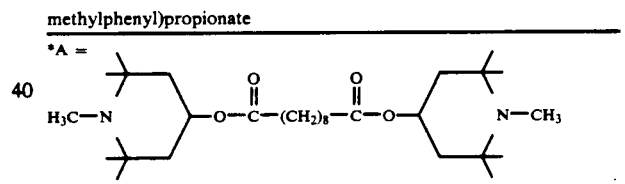

APPLICATION EXAMPLE 2

The following samples listed in Table 4 were prepared and tested as described in Application Example 1:

TABLE 4

| Stabilizer | Concentration [%] | YI of ASTM D 1925 0 h | YI of ASTM D 1925 96 h |
|---|---|---|---|
| 4.1 Control | — | 5.0 | 32.5 |
| 4.2 Compound of Example 6 | 0.5 | | |
| +A | 0.5 | 4.6 | 21.0 |
| +B* | 0.25 | | |
| 4.3 Compound of Example 8 | 0.5 | | |
| +A | 0.5 | 2.6 | 22.6 |
| +B | 0.25 | | |
| 4.4 Compound of Example 14 | 0.5 | | |
| +A | 0.5 | 4.7 | 19.1 |
| +B | 0.25 | | |
| 4.5 Compound of Example 22 | 0.5 | | |
| +A | 0.5 | 4.0 | 18.5 |
| +B | 0.25 | | |

B* = Mixture of 1 part by weight of α-tocopherol and 10 parts by weight of tris(nonylphenyl) phosphite

APPLICATION EXAMPLE 3

Volatility of stabilizers in the clearcoat of a two-layer metallic system

Each stabilizer was stirred in a 0.4 g amount into 55.6 g of a ready-to-spray clearcoating formulation comprising 1,500 parts of acrylate baking finish and 167 parts of xylene until solution was complete.

The ready-prepared coating solution was drawn down on quartz glass (layer thickness about 40 μm) and baked at 140° C. for 5 hours. To determine the loss of UV absorber during baking, absorption spectra were recorded before and after baking, and the loss was determined from the decrease in optical density at the absorption maximum.

TABLE 5

| Stabilizer | Percentage loss after 5 h at 140° C. |
|---|---|
| 5.1 4-Octyloxy-2-hydroxy-benzophenone | 18 |
| 5.2 2-(3',5'-di-t-amyl-2'-hydroxyphenyl)benzotriazole | 83 |
| 5.3 2-(3',5'-di-α,α'-dimethyl-2'-hydroxyphenyl)-benzotriazole | 5 |
| 5.4 Compound of Example 1 | 5 |
| 5.5 Compound of Example 2 | 1.7 |
| 5.6 Compound of Example 4 | 2.8 |
| 5.7 Compound of Example 8 | 5.7 |
| 5.8 Compound of Example 9 | 6.3 |
| 5.9 Compound of Example 10 | 0.5 |
| 5.10 Compound of Example 11 | 2.4 |
| 5.11 Compound of Example 14 | 6.5 |
| 5.12 Compound of Example 17 | 3.3 |

We claim:

1. A compound of the formula (I)

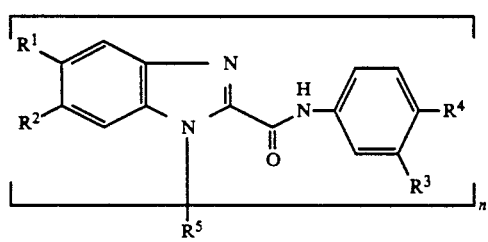

where
$R^1$ and $R^2$ are each independently of the other H, Cl, $C_1$–$C_4$-alkyl, $C_1$–$C_4$-alkoxy, unsubstituted or $C_1$–$C_4$-alkyl- or $C_1$–$C_4$-alkoxy-substituted phenyl or $C_7$–$C_9$-phenylalkyl, $R^3$ and $R^4$ are each independently of the other H, $C_1$–$C_{18}$-alkyl, $C_3$–$C_{18}$-alkyl which is interrupted one or more times by —O—, $C_1$–$C_{18}$-alkoxy, $C_4$–$C_{18}$-alkoxy which is interrupted one or more times by —O—, unsubstituted or $C_1$–$C_4$-alkyl- or $C_1$–$C_4$-alkoxy-substituted phenyl, $C_7$–$C_{15}$-phenylalkyl, phenoxy, $C_7$–$C_{15}$-phenylalkyloxy, $C_1$–$C_{12}$-alkylcarbonylamino, benzoylamino, $C_1$–$C_{12}$-alkanoyloxy or benzoyloxy, or $R^3$ and $R^4$ together are methylenedioxy or ethylenedioxy, n is 1 or 2 and $R^5$ is (a)—when n is 1 —$C_5$–$C_{18}$-alkyl, $C_2$–$C_{10}$-hydroxyalkyl, $C_5$–$C_{12}$-cycloalkyl, $C_2$–$C_{18}$-alkenyl, which cycloalkyl and alkenyl may be substituted by OH, $C_3$–$C_{18}$-alkyl which is interrupted one or more times by —O—, unsubstituted or $C_1$–$C_4$-alkyl- or $C_1$–$C_4$-alkoxy-substituted $C_8$–$C_{15}$-phenylalkyl or a radical of the formula

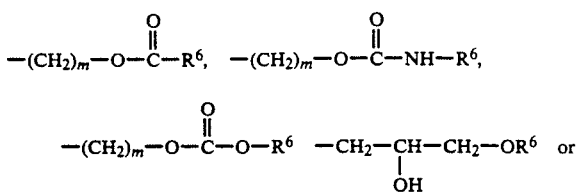

where
m is from 2 to 4 and
$R^6$ is $C_1$–$C_{18}$-alkyl, $C_2$–$C_{18}$-alkenyl, $C_5$–$C_{12}$-cycloalkyl, $C_7$–$C_{15}$-phenylalkyl, unsubstituted or $C_1$–$C_4$-alkyl- or $C_1$–$C_4$-alkoxy-substituted phenyl or naphthyl, or (b)—when n is 2-$C_2$–$C_{10}$-alkylene, $C_5$–$C_{12}$-cycloalkylene, which alkylene and cycloalkylene may be substituted by —OH, $C_4$–$C_{12}$-alkenylene, $C_4$–$C_8$-alkylene which is interrupted one or more times by —O—, or a radical of the formula

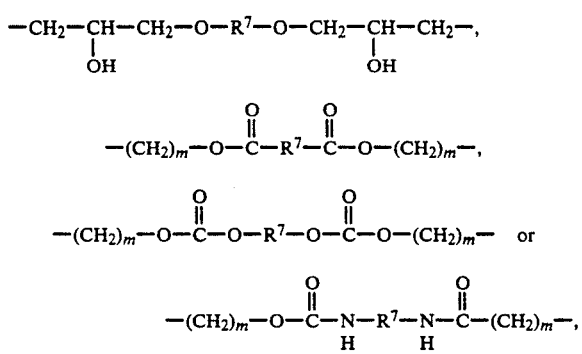

where
$R^7$ is $C_2$–$C_8$-alkylene, $C_2$–$C_8$-alkenylene, $C_5$–$C_{12}$-cycloalkylene, unsubstituted or $C_1$–$C_4$-alkyl- or $C_1$–$C_4$-alkoxysubstituted phenylene, naphthylene, diphenylene or a radical of the formula

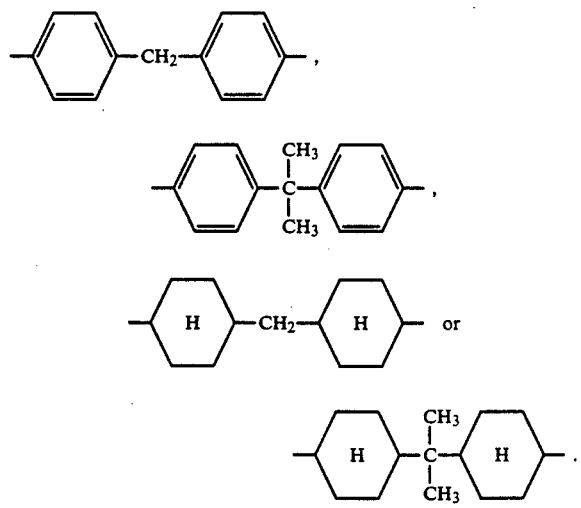

2. A compound as claimed in claim 1, wherein in the formula $R^1$ and $R^2$ are each independently of the other H, $C_1$-$C_4$-alkyl, $C_1$-$C_4$-alkoxy or $C_7$-$C_9$-phenylalkyl, $R^3$ and $R^4$ are each independently of the other H, $C_1$-$C_{12}$-alkyl, $C_1$-$C_{12}$-alkoxy, $C_3$-$C_{10}$-alkyl which is interrupted one or more times by —O—, $C_4$-$C_{12}$-alkoxy which is interrupted one or more times by —O—, $C_7$-$C_9$-phenylalkyl, $C_7$-$C_9$-phenylalkoxy, phenoxy, $C_1$-$C_{12}$-alkylcarbonylamino, benzoylamino, $C_1$-$C_{12}$-alkanoyloxy or benzoyloxy, n is 1 and $R^5$ is $C_5$-$C_{18}$-alkyl, $C_2$-$C_{10}$-hydroxyalkyl, $C_5$-$C_{12}$-cycloalkyl, $C_2$-$C_{18}$-alkenyl, $C_3$-$C_{18}$-alkyl which is interrupted one or more times by —O—, $C_8$-$C_{15}$-phenylalkyl or a radical of the formula

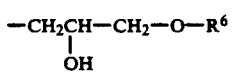

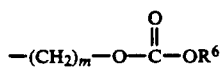

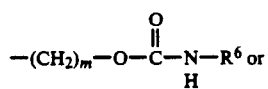

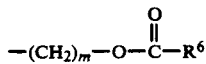

where m is 2, 3 or 4 and $R^6$ is $C_1$-$C_{18}$-alkyl, $C_2$-$C_{18}$-alkenyl, $C_5$-$C_{12}$-cycloalkyl, unsubstituted or $C_1$-$C_4$-alkyl-or $C_1$-$C_4$-alkoxysubstituted $C_7$-$C_{15}$-phenylalkyl, unsubstituted or $C_1$-$C_4$-alkyl- or $C_1$-$C_4$-alkoxy-substituted phenyl or $C_1$-$C_4$-alkyl- or $C_1$-$C_4$-alkoxy-substituted naphthyl.

3. A compound as claimed in claim 1, wherein in the formula $R^1$ and $R^2$ are each independently the other H, $C_1$-$C_4$-alkyl, $C_1$-$C_4$-alkoxy or $C_7$-$C_9$-phenylalkyl, $R^3$ and $R^4$ are each independently of the other H, $C_1$-$C_{12}$-alkyl, $C_1$-$C_{12}$-alkoxy, $C_4$-$C_{12}$-alkoxy which is interrupted one or more times by —O—, $C_7$-$C_9$-phenylalkyl, $C_7$-$C_9$-phenylalkoxy, phenoxy, $C_1$-$C_{121}$-alkylcarbonylamino, benzoylamino, $C_1$-$C_{12}$-alkanoyloxy or benzoyloxy, n is 2 and $R^5$ is $C_2$$C_{10}$-alkylene or hydroxyalkylene, unsubstituted or —OH—substituted $C_5$-$C_{12}$-cycloalkylene, $C_4$-$C_{12}$-alkenylene, $C_4$-$C_8$-alkylene which is interrupted one or more times by —O— or a radical of the formula

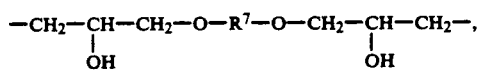

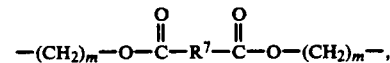

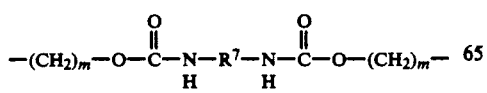

m is 2, 3 or 4 and is $C_2$-$C_8$-alkylene, $C_2$-$C_8$-alkenylene, $C_5$-$C_{12}$-cycloalkylene, unsubstituted or $C_1$-$C_4$-alkyl- or $C_1$-$C_4$-alkoxysubstituted phenylene, naphthylene, diphenylene,

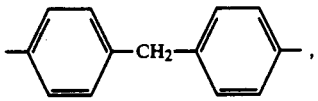

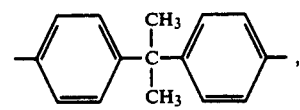

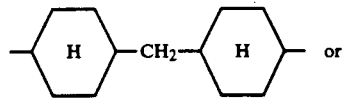 or

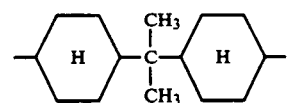

4. A compound as claimed in claim 1, wherein in the formula (I) $R^1$ and $R^2$ are each independently of the other H, $C_1$-$C_4$-alkyl, methoxy, ethoxy, benzyl, phenylethyl, α-methylbenzyl or α,α'-dimethylbenzyl, $R^3$ is H, $R^4$ is $C_1$-$C_{12}$-alkyl, $C_1$-$C_{12}$-alkoxy, phenoxy, $C_7$-$C_9$-phenylalkoxy, $C_1$-$C_{12}$-alkylcarbonylamino, benzoylamino, $C_1$-$C_{12}$-alkanoyloxy or benzoyloxy, n is 1 and $R^5$ is $C_5$-$C_{18}$-alkyl, $C_2$-$C_8$-hydroxyalkyl, $C_2$-$C_{18}$-alkenyl, $C_3$-$C_{10}$-alkyl which is interrupted one or more times by —O—, unsubstituted or methyl-, ethyl- or methoxysubstituted $C_8$ or $C_9$-phenylalkyl or a radical of the formula

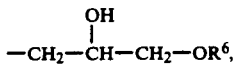

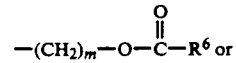 or

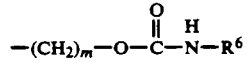

where m is 2, 3 or 4 and $R^6$ is $C_1$-$C_{18}$-alkyl, $C_2$-$C_{18}$-alkenyl, $C_7$-$C_9$-phenylalkyl, unsubstituted or $C_1$-$C_4$-alkyl- or $C_1$-$C_4$-alkoxysubstituted phenyl or $C_1$-$C_4$-alkyl- or $C_1$-$C_4$-alkoxysubstituted naphthyl.

5. A compound as claimed in claim 2, wherein in the formula (I) $R^1$ and $R^2$ are each independently of the other H, $C_1$-$C_4$-alkyl, methoxy, ethoxy, benzyl, phenylethyl, α-methylbenzyl or α,α'-dimethylbenz-yl, $R^3$ is H, $R^4$ is $C_1$-$C_{12}$-alkyl, $C_1$-$C_{12}$-alkoxy, phenoxy, $C_7$-$C_9$-phenylalkoxy, $C_1$-$C_{12}$-alkylcarbonylamino, benzoylamino, $C_1$-$C_{12}$-alkanoyloxy or benzoyloxy, n is 1 and $R^5$ is $C_5$-$C_{18}$-alkyl, $C_2$-$C_8$-hydroxyalkyl, $C_2$-$C_{18}$-alkenyl, $C_3$-$C_{10}$-alkyl which is interrupted one or more times by —O—, unsubstituted or methyl-, ethyl- or methoxysubstituted $C_8$ or $C_9$-phenylalkyl or a radical of the formula

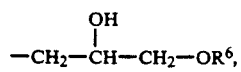

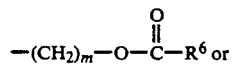

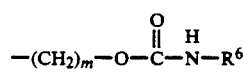

where
m is 2, 3 or 4 and
$R^6$ is $C_1$-$C_{18}$alkyl, $C_2$-$C_{18}$-alkenyl, $C_7$-$C_9$-phenylalkyl, unsubstituted or $C_1$-$C_4$ alkyl- or $C_1$-$C_4$-alkoxy-substituted phenyl or $C_1$-$C_4$-alkyl- or $C_1$-$C_4$-alkoxysubstituted naphthyl.

6. A compound as claimed in claim 1, wherein in the formula
$R^1$ and $R^2$ are each independently of the other H, $C_1$-$C_4$-alkyl, methoxy, ethoxy, benzyl, α-methylbenzyl or α,α-dimethylbenzyl,
$R^3$ is H,
$R^4$ is $C_1$-$C_{12}$-alkyl, $C_1$-$C_{12}$-alkoxy, phenoxy, $C_7$-$C_9$-phenylalkoxy, $C_1$-$C_{12}$-alkylcarbonylamino, benzoylamino, $C_1$-$C_{12}$-alkanoyloxy or benzoyloxy,
n is 2 and
$R^5$ is $C_2$-$C_{10}$-alkylene, $C_4$-$C_{12}$-alkenylene, $C_4$-$C_8$-alkylene which is interrupted one or more times by —O—, or a divalent radical of the formula

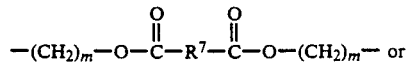

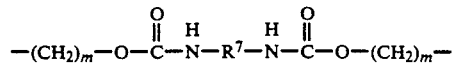

where
m is 2, 3 or 4 and
$R^7$ is $C_2$-$C_8$-alkylene, $C_2$-$C_8$-alkenylene, 1,3- or 1,4-phenylene or diphenylene.

7. A compound as claimed in claim 3, wherein in the formula
$R^1$ and $R^2$ are each independently of the other H, $C_1$-$C_4$-alkyl, methoxy, ethoxy, benzyl, α-methylbenzyl or α,α-dimethylbenzyl,
$R^3$ is H,
$R^4$ is $C_1$-$C_{12}$-alkyl, $C_1$-$C_{12}$-alkoxy, phenoxy, $C_7$-$C_9$-phenylalkoxy, $C_1$-$C_{12}$-alkylcarbonylamino, benzoylamino, $C_1$-$C_{12}$-alkanoyloxy or benzoyloxy,
n is 2 and
$R^5$ is $C_2$-$C_{10}$-alkylene, $C_4$-$C_{12}$-alkenylene, $C_4$-$C_8$-alkylene which is interrupted one or more times by —O— or a divalent radical of the formula

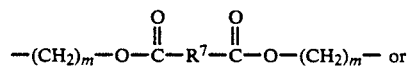

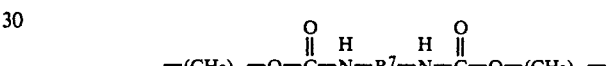

where
m is 2, 3 or 4 and
$R^7$ is $C_2$-$C_8$-alkylene, $C_2$-$C_8$-alkenylene, 1,3- or 1,4-phenylene or diphenylene.

* * * * *